United States Patent
Govari et al.

(10) Patent No.: US 9,247,985 B2
(45) Date of Patent: Feb. 2, 2016

(54) TEST JIG FOR ABLATOR

(75) Inventors: Assaf Govari, Haifa (IL); Andres Claudio Altmann, Haifa (IL); Yaron Ephrath, Karkur (IL); Tom Sagie Stern, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1224 days.

(21) Appl. No.: 13/191,842

(22) Filed: Jul. 27, 2011

(65) Prior Publication Data

US 2013/0027069 A1 Jan. 31, 2013

(51) Int. Cl.
*G01K 15/00* (2006.01)
*A61B 18/12* (2006.01)
*A61B 18/00* (2006.01)

(52) U.S. Cl.
CPC ... *A61B 18/1233* (2013.01); *A61B 2018/00642* (2013.01); *A61B 2018/00702* (2013.01); *A61B 2018/00714* (2013.01); *A61B 2018/00755* (2013.01); *A61B 2018/00791* (2013.01); *A61B 2018/00821* (2013.01); *A61B 2018/00875* (2013.01)

(58) Field of Classification Search
USPC .......................................................... 374/1
See application file for complete search history.

(56) References Cited

U.S. PATENT DOCUMENTS

| | | | |
|---|---|---|---|
| 4,934,365 A * | 6/1990 | Morgenthaler | A61N 1/403 607/101 |
| 5,066,140 A | 11/1991 | Beran | |
| 5,197,479 A * | 3/1993 | Hubelbank et al. | 600/508 |
| 5,443,463 A | 8/1995 | Stern et al. | |
| 5,716,381 A * | 2/1998 | Reggiardo | 607/8 |
| 5,769,847 A | 6/1998 | Panescu et al. | |
| 7,238,184 B2 | 7/2007 | Megerman et al. | |
| 2006/0217707 A1 | 9/2006 | Daniel et al. | |
| 2008/0071263 A1 * | 3/2008 | Blaha | A61B 18/1233 606/35 |
| 2011/0066147 A1 * | 3/2011 | He et al. | 606/33 |
| 2011/0218526 A1 * | 9/2011 | Mathur | A61B 18/1206 606/33 |

FOREIGN PATENT DOCUMENTS

WO  WO 96/00036 A1  1/1996

OTHER PUBLICATIONS

Extended European Search Report dated Nov. 5, 2012 from related European Application No. 12177947.4.
Biosense Webster, Inc., Inventors: Assaf Govari et al. filed on Dec. 16, 2010 as U.S. Appl. No. 12/969,684—pending.

* cited by examiner

*Primary Examiner* — Max Noori
*Assistant Examiner* — Nasir U Ahmed
(74) *Attorney, Agent, or Firm* — Louis J. Capezzuto

(57) ABSTRACT

In techniques for testing and calibrating an ablator, a tissue probe emulator is connectable to a tissue ablator being tested. The emulator includes a temperature sensor, a thermoelectric unit operative to vary a temperature sensed by the temperature sensor, an adjustable electrical load, electrical control circuitry connected to the thermoelectric unit and the electrical load and operative to independently adjust the electrical load and an output of the thermoelectric unit. The emulator conveys signals emitted by the temperature sensor to the tissue ablator and conveys an ablation energy output of the tissue ablator to the electrical load.

17 Claims, 5 Drawing Sheets

TEST JIG FOR ABLATOR

BACKGROUND OF THE INVENTION

1. Field of the Invention

This invention relates to medical devices. More particularly, this invention relates to a test harness for evaluation of control circuitry in medical devices that perform tissue ablation.

2. Description of the Related Art

Ablation of body tissue using electrical energy is known in the art. The ablation is typically performed by applying alternating currents to the electrodes, for example radiofrequency (RF) energy, at a sufficient power to destroy target tissue. Typically, the electrodes are mounted on the distal tip of a catheter, which is inserted into a subject. The distal tip may be tracked in a number of different ways known in the art, for example by measuring magnetic fields generated at the distal tip by coils external to the subject.

A known difficulty in the use of radiofrequency energy for tissue ablation, e.g., cardiac tissue ablation, is controlling local heating of tissue. Precise control of the amount of RF energy applied by the catheter electrode is important in achieving consistent therapeutic results while avoiding excessive injury to surrounding tissues.

Self-regulating tissue ablators have been proposed to achieve the desired control. For example, PCT International Publication WO9600036 discusses ablation of body tissue in which ablating energy is conveyed individually to multiple emitters in a sequence of power pulses. The temperature of each emitter is periodically sensed and compared to a desired temperature established for all emitters to generate a signal individually for each emitter based upon the comparison. The power pulse to each emitter is individually varied, based upon the signal for that emitter to maintain the temperatures of all emitters essentially at the desired temperature during tissue ablation.

SUMMARY OF THE INVENTION

There is provided according to embodiments of the invention an apparatus for testing and calibrating an ablator, including a tissue probe emulator connectable to a tissue ablator being tested, the emulator including a temperature sensor, a thermoelectric unit operative to vary a temperature sensed by the temperature sensor, an adjustable electrical load, electrical control circuitry connected to the thermoelectric unit and the electrical load and operative to independently adjust the electrical load and an output of the thermoelectric unit, and an adapter, connectable to a receptacle of the ablator and coupled to convey signals emitted by the temperature sensor to the tissue ablator and to convey an ablation energy output of the tissue ablator to the electrical load.

A further aspect of the apparatus includes a meter for measuring an electrical output of the tissue ablator.

According to an additional aspect of the apparatus, the electrical load includes a plurality of resistive elements has respective resistance values, and a plurality of relays associated with respective ones of the resistive elements, wherein the relays are operative, responsively to signals of the electrical control circuitry, to respectively connect and disconnect their associated resistive elements.

According to another aspect of the apparatus, the resistive elements are connectable relative to a common reference to emulate a unipolar electrode and are connectable relative to one another to emulate a bipolar electrode.

According to one aspect of the apparatus, the electrical load includes a plurality of variable resistance channels, each including a plurality of resistive elements has respective resistance values, and a plurality of relays associated with respective ones of the resistive elements, wherein the relays are operative, responsively to signals of the electrical control circuitry, to respectively connect and disconnect their associated resistive elements, and a switch for completing a circuit between a selected one of the variable resistance channels to the tissue ablator.

According to still another aspect of the apparatus, the electrical control circuitry includes a microcontroller, and switching transistors connected to the microcontroller and respective ones of the relays, the transistors is responsive to relay control signals of the microcontroller for enabling and disabling the relays.

Yet another aspect of the apparatus includes a computing device linked to the electrical control circuitry. The computing device is programmed to cause the electrical control circuitry to execute a predetermined sequence of independently adjusting the electrical load and the output of the thermoelectric unit, and a receiver-transmitter for intercommunicating information between the microcontroller and the computing device.

According to one aspect of the apparatus, the electrical load includes a plurality of resistive elements having respective resistance values, and electrical connectors associated with respective ones of the resistive elements for connecting selected ones of the resistive elements to the tissue ablator.

Other embodiments of the invention provide methods for operating apparatus, including the above-described apparatus.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

The RF electrical current applied by an ablator may be controlled by feedback based on the tissue temperature and delivered power. Commonly assigned application Ser. No. 12/969,684 filed on Dec. 16, 2010, entitled "System for Controlling Tissue Ablation Using Temperature Sensors", which is herein incorporated by reference, describes a control technique of this sort.

As part of the process of producing an ablator (including the RF power supply and control circuits), the ablator is conventionally connected to a catheter and tested in operation. For this purpose, the catheter electrode is connected to a dummy load, and the ablator output is measured as a function of varying load and possibly other conditions. This arrangement does not permit the temperature response of the ablator control circuits to be fully tested, however, because the heat generated in the load and measured by the temperature sensor in the catheter will generally not reflect the actual temperature response of biological tissue on which the ablator is meant to be used.

Figure 1:
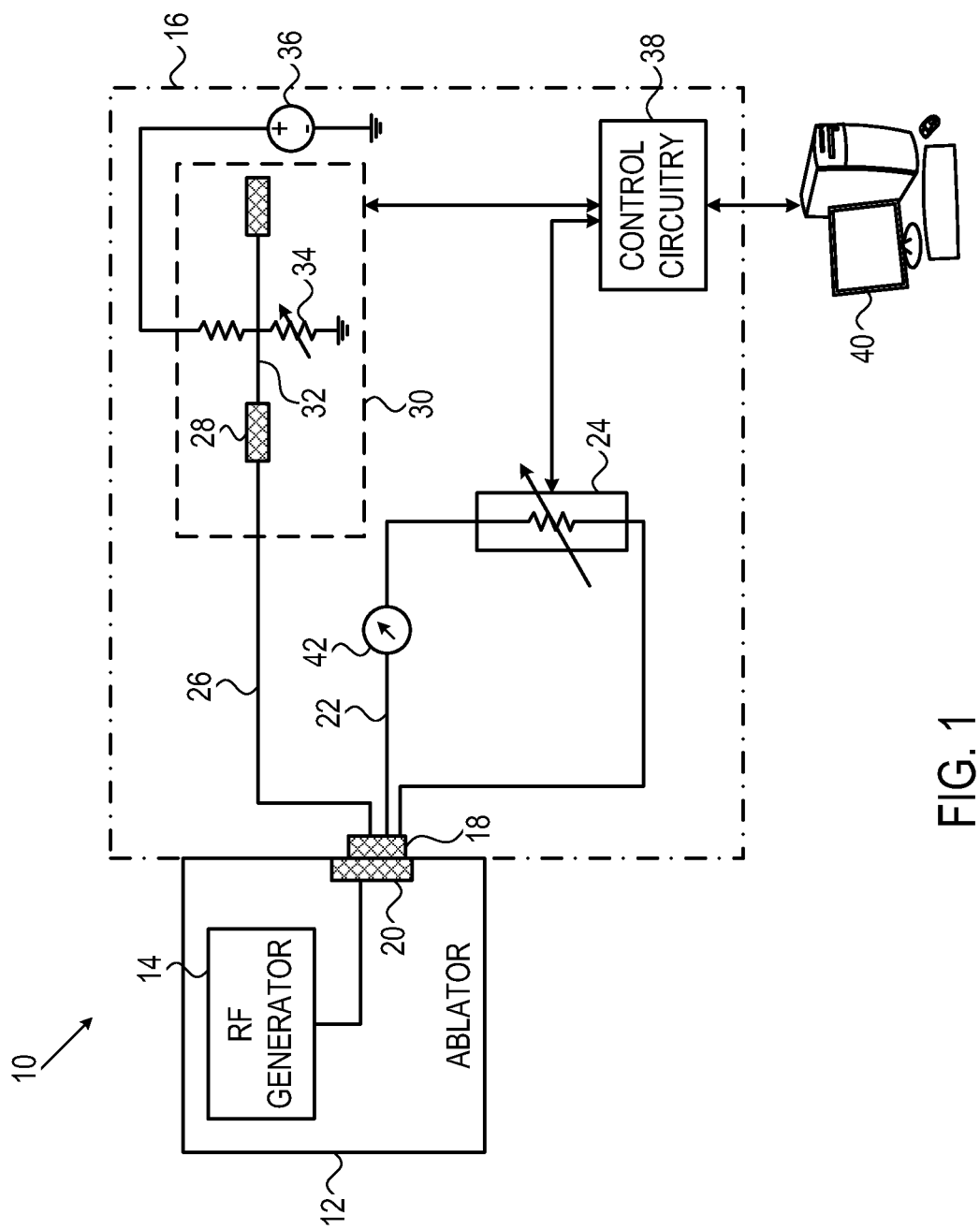
FIG. 1 is a schematic diagram of a test harness for a tissue ablator, which is constructed and operative in accordance with an embodiment of the invention.

Turning now to the drawings, reference is initially made to FIG. 1, which is a schematic diagram of a jig or test harness 10 for a testing and calibrating a tissue ablator, which is constructed and operative in accordance with an embodiment of the invention. The test harness 10 is connected to a tissue ablator 12 that is being evaluated. The ablator 12 includes at least one RF power generator 14.

In practice, the ablator 12 under test is a component of a system that includes an invasive probe or catheter, such as a cardiac catheter (not shown). The test harness 10 includes a catheter emulator 16, and an adaptor 18, which plugs into a catheter receptacle 20 of the ablator 12 but then splits off into two end-units: A power lead 22 connects the RF output of the ablator 12 to an adjustable electric load 24, while a temperature lead 26 connects the temperature sensing input of the ablator 12 to a modified temperature sensor 28 (such as a thermocouple). The temperature sensor 28 is attached to or embedded in a thermoelectric (T/E) unit 30. The thermoelectric unit 30 may be realized by disassembling a thermocouple, making an internal connection to a voltage divider 32 having a variable resistor 34, supplied by a voltage source 36. By adjusting the resistor 34, the output of the thermocouple can be controlled by control circuitry 38 to simulate a desired temperature. Alternatively, the thermoelectric unit 30 may be a Peltier heater/cooler, which operates to vary the temperature of the environment sensed by the temperature sensor 28.

Electrical control circuitry 38 connected to the temperature sensor 28 and thermoelectric unit 30. During testing of the ablator 12, the control circuitry 38 communicates control signals separately and independently to the electric load 24 and the thermoelectric unit 30, causing the thermal environment of the temperature sensor 28 to vary according to a predetermined testing sequence.

For example the temperature sensor 28 may initially register 38° C. and progress to 44° C. while the power varies up to 25 W per channel.

In an alternative testing sequence, the temperature sensor 28 may initially be set to register 38° C. and progress to an upper temperature limit of 47° C., with oscillations of +/−2° C., during which the power may reach a target of 25 W and then drop, so as to maintain the temperature readings below 47° C.

In yet another alternative testing sequence, designed for testing safety of the ablator, the temperature sensor 28 may initially be set to register 47° C. and progress to 80° C. It is expected that the system will issue an alert indicating an abnormally high temperature and will produce control signals intended to stop the ablation.

The control circuitry 38 is optionally linked to a host device 40, which can be a general purpose computer suitably programmed with the testing sequence and adapted to regulate the control circuitry 38. A monitor, for example a power meter 42 measures the power output of the ablator 12 as the load and temperature vary. In this manner the response of the ablator 12 to the load 24 and the temperature sensed by the temperature sensor 28 can be fully tested over the full range of conditions that may be encountered clinically. In addition automated functions and safety limits that are incorporated in the ablator 12 may be tested. For example, it may be verified that exceeding a predetermined maximum temperature causes the ablator's power output to drop. Several other practical limiting conditions are described in the above noted Application No. (DKP 1001-1113; BIO-5271).

Figure 2:
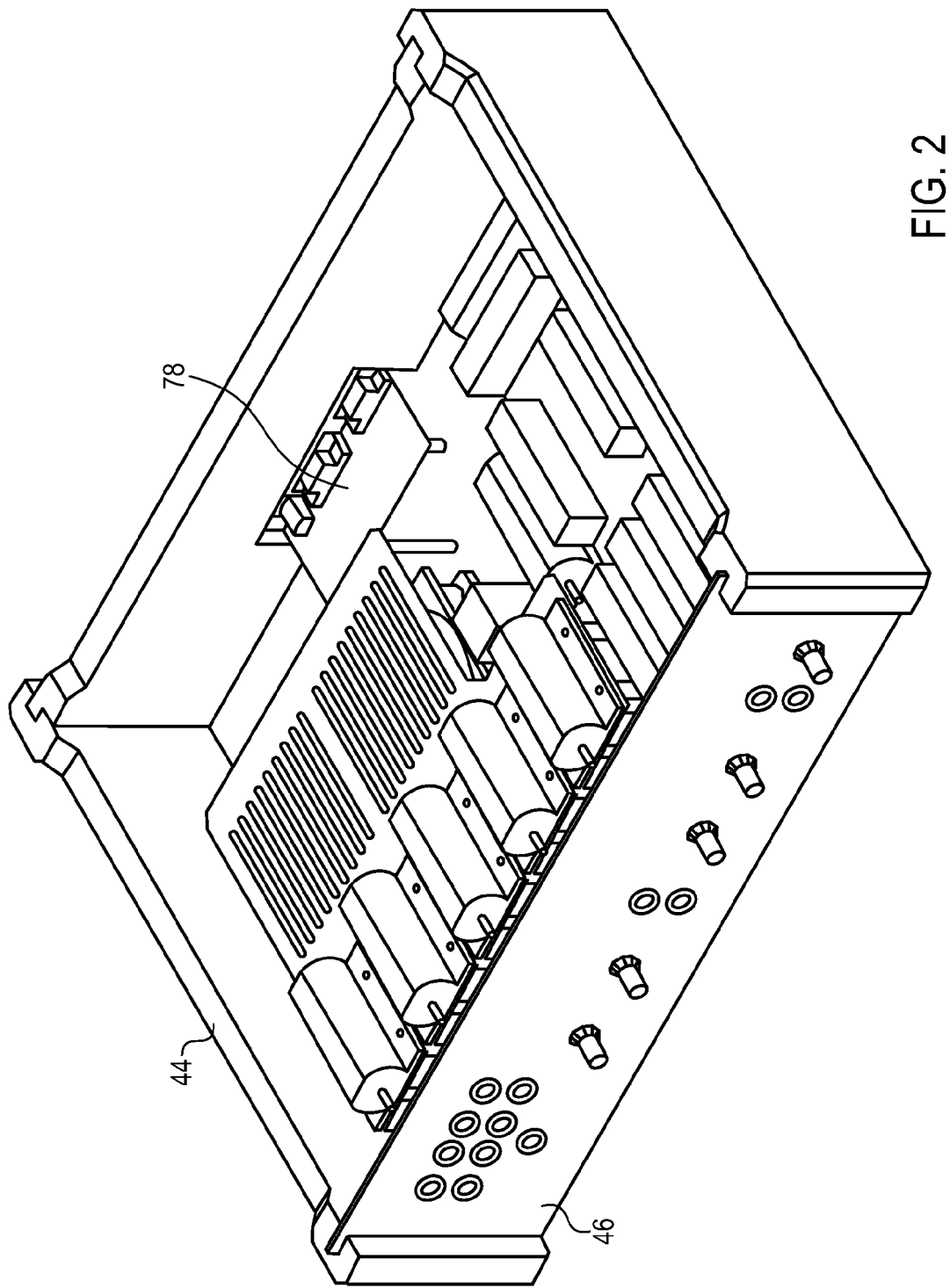
FIG. 2 is an angular view of a test harness, in accordance with an embodiment of the invention.

Reference is now made to FIG. 2, which is an angular view of a box 44 with the top cover removed. A front panel 46 has banana and coaxial connectors, e.g., BNC connectors to receive inputs for the channels as well a feed through connection for a power metering device and "return" connections. The box 44 may be configured for testing and/or calibrating several ablators concurrently by replicating the circuitry or by time-multiplexing a single set of components.

Figure 3:
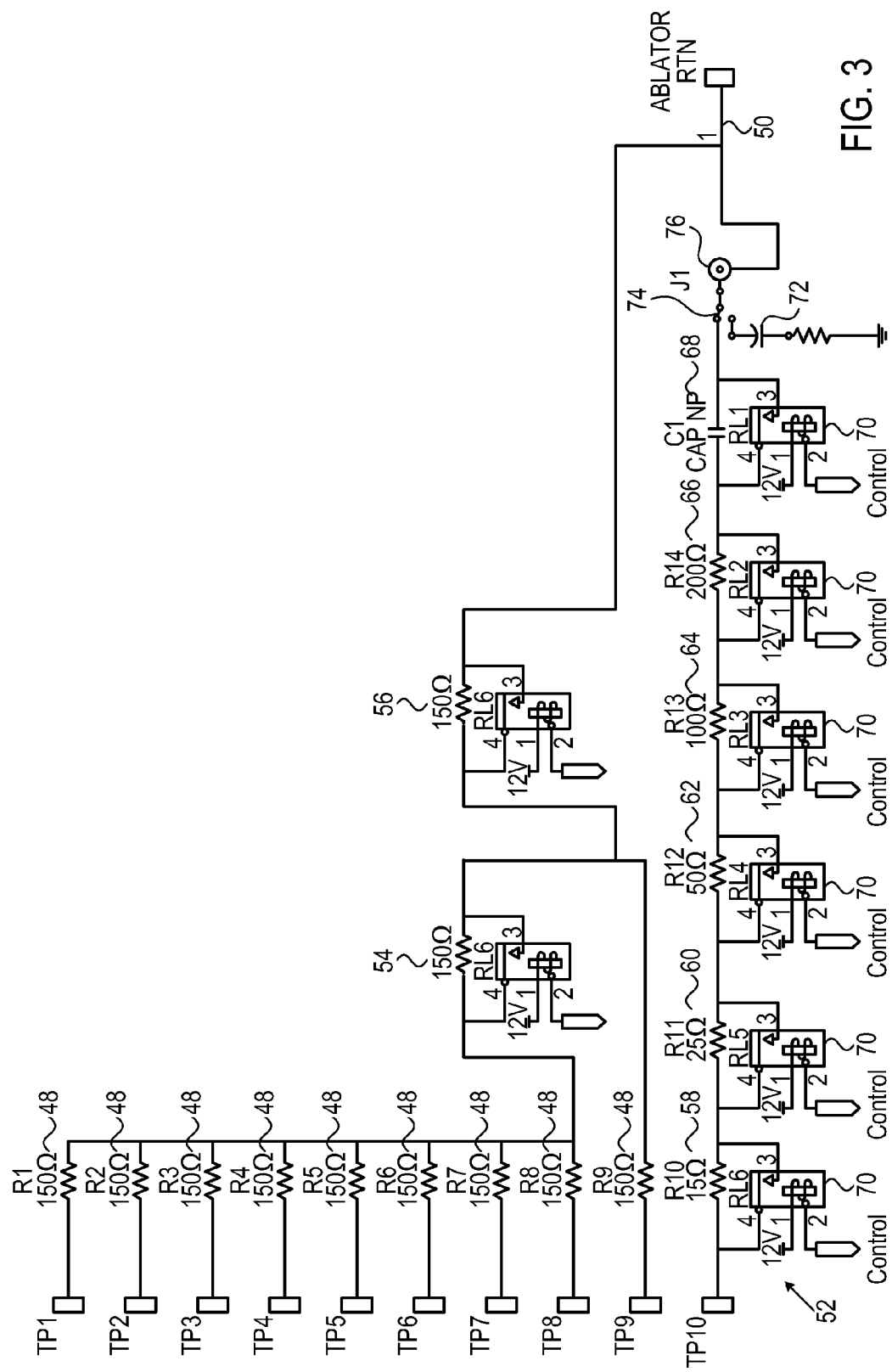
FIG. 3 is an electrical schematic of circuitry of the test harness shown in FIG. 2, which is constructed and operative in accordance with an embodiment of the invention.

Reference is now made to FIG. 3, which is an electrical schematic of circuitry of the test harness 10 (FIG. 1) in accordance with an embodiment of the invention. Nine fixed resistors 48 (R1-R9) are connected to the same return path 50 as variable channel 52. The return path of the resistors 48 can be interrupted by two relays 54, 56.

The resistors 48 comprising the fixed channels are Arcol NHS100 series 150Ω non inductive power resistors. The variable channel 52 also uses the same type, resistors 58, 60, 62, 64, 66 having 15, 25, 50, 100 and 200Ω values, respectively. Additionally there is a high-voltage 0.0033 µF polypropylene capacitor 68. The capacitor 68 is useful for simulating the tissue-electrode interface, which is not purely resistive in nature. The resistors 58, 60, 62, 64, 66 are each wired in parallel with high-voltage 3 Amp "hot-switchable" reed relays 70 that can short each resistor, thus bypassing it. This method can be used to introduce various resistive loads to the power generator 14 (FIG. 1). A calibration circuit 72 may be enabled using switch 74. Furthermore, by varying the operation of the relays 54, 56, 70, the resistances may be connected to one another so as to emulate a bipolar electrode, or connected to a common point so as to emulate a unipolar electrode.

A "feed through" BNC connector 76 is in series with the variable channel, but not the resistors 48. The BNC connector 76 allows for connection of an external power metering device (not shown), which is used to calculate power fed through the variable channel 52. If external power metering is not needed, the BNC connector 76 is shorted using a shorting plug (not shown).

Figure 4:
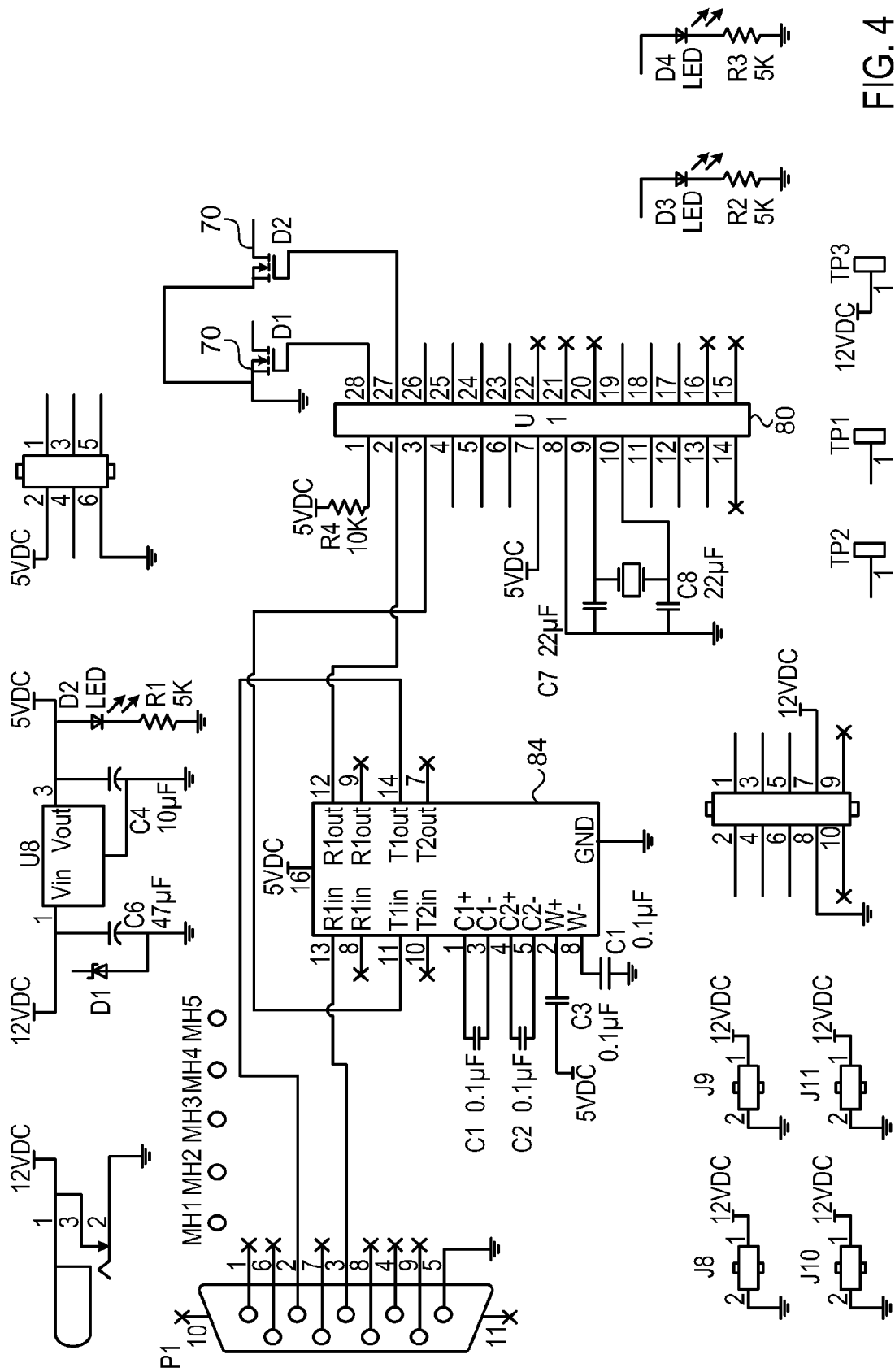
FIG. 4 is an electrical schematic of control circuitry of the test harness shown in FIG. 2, which is constructed and operative in accordance with an embodiment of the invention.

Reference is now made to FIG. 4, which is an electrical schematic of circuitry on a printed circuit board 78 that is constructed and operative in accordance with an embodiment of the invention. The relays 70 (corresponding to relays shown in FIG. 3) are all controlled via a microcontroller unit 80 that switches MOSFET transistors 82 (Model BSS138; available from Fairchild Semiconductor Corporation, 3030 Orchard Parkway, San Jose Calif. 95134), to enable and disable the various relays as needed. The microcontroller unit 80 may be a model ATMEGA168 self-programming flash program memory (available from Atmel Corporation, 2325 Orchard Parkway, San Jose, Calif. 95131), that can communicate with a host computer via a Universal Asynchronous Receiver-Transmitter (UART) using a MAX232 voltage converter 84. The UART settings are: 9600 baud, 8 bit data, 1 start/stop bit, no parity. Requests are sent in ASCII. Further details of the communication protocol are given in Table 1.

TABLE 1

| Relay | Request ON/OFF |
|---|---|
| 10K | A/a |
| 25K | B/b |
| 50K | C/c |
| 100K | D/d |
| 200K | E/e |
| CAP | F/f |
| SHRT_RTN1 | G/g |
| SHRT_RTN2 | H/h |
| IPA1 | I/i |
| IPA2 | J/j |
| IPB1 | K/k |
| IPB2 | L/l |

A request byte is expected, followed by a confirmation byte. A command to the microcontroller unit 80 consists of an upper case or lower case letter (A-L; a-l) to enable and disable a relay, respectively. The request is echoed to the host for comparison. If the request is confirmed by the host, a confirmation command is expected in the form of the letter 'z'. After which the required relay is switched as appropriate, and 'ok' will be sent to the host as confirmation that the command has been serviced, and as an indication that a new request can be sent. An error condition, i.e., failure to successfully service the command is indicated by returning an 'e' character to the host. The microcontroller unit 80 then awaits a new command.

Alternate Embodiment

Figure 5:
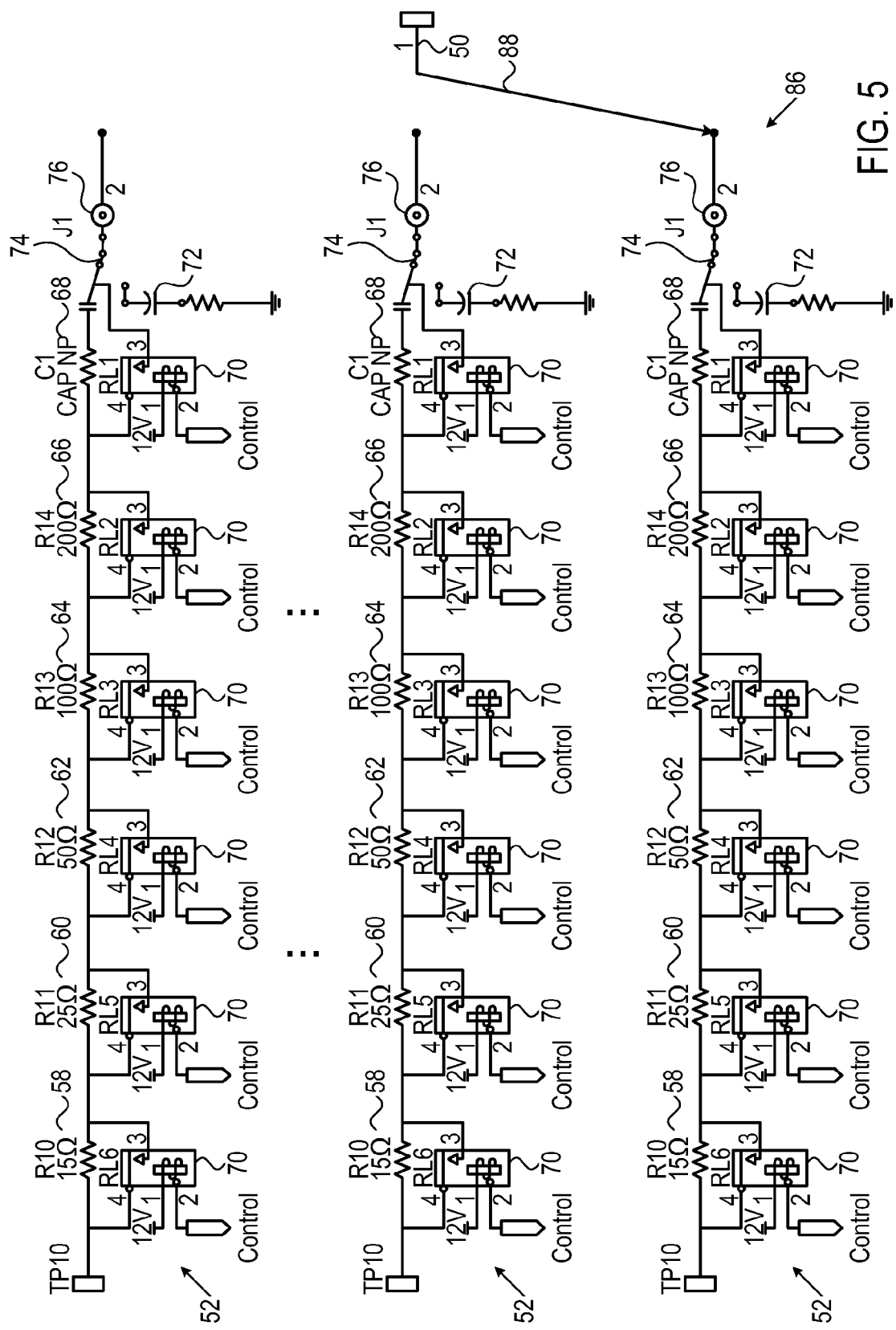
FIG. 5 is an electrical schematic of circuitry of the test harness shown in FIG. 2, which is constructed and operative in accordance with an alternate embodiment of the invention.

Reference is now made to FIG. 5, which is an electrical schematic of circuitry 86 of the test harness shown in FIG. 2, which is constructed and operative in accordance with an alternate embodiment of the invention. The circuitry differs from that shown in FIG. 3 in that instead of having one variable channel 52 and multiple fixed resistors 48, there are now a plurality of variable channels, the resistances of which are all configurable using the relays 70. While the actual values of the resistances in the variable channels are shown in FIG. 5 as identical, this is not necessarily the case. Indeed, the values and the number of resistances and relays 70 may vary independently in different channels, according to the needs of a particular application.

The ablator return path 50 is switchable among the different variable channels 52, using a switch 88. The circuitry 86 facilitates evaluation and calibration of any number of channels in the same session.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for testing and/or calibrating an ablator, comprising:
a tissue probe emulator connectable to a tissue ablator being tested, the emulator comprising:
a temperature sensor;
a thermoelectric circuit connected to the temperature sensor and operative to vary an output temperature of the thermoelectric circuit sensed by the temperature sensor;
an electrical load configured to be adjustable in response to control signals;
electrical control circuitry connected to the thermoelectric unit and the electrical load and operative to independently apply control signals to adjust the electrical load and the output of the thermoelectric circuit; and
an adapter, connectable to a receptacle of the ablator and coupled to convey signals emitted by the temperature sensor to the tissue ablator and to convey an ablation energy output of the tissue ablator to the electrical load.

2. The apparatus according to claim 1, further comprising a meter for measuring an electrical output of the tissue ablator.

3. The apparatus according to claim 1, wherein the electrical load comprises:
a plurality of resistive elements having respective resistance values; and
a plurality of relays associated with respective ones of the resistive elements, wherein the relays are operative, responsively to signals of the electrical control circuitry, to respectively connect and disconnect their associated resistive elements.

4. The apparatus according to claim 3, wherein the resistive elements are connectable relative to a common reference to emulate a unipolar electrode and are connectable relative to one another to emulate a bipolar electrode.

5. The apparatus according to claim 3, wherein the electrical control circuitry comprises:
a microcontroller; and
switching transistors connected to the microcontroller and respective ones of the relays, the transistors being responsive to relay the control signals of the microcontroller for enabling and disabling the relays.

6. The apparatus according to claim 5, further comprising:
a computing device linked to the electrical control circuitry, the computing device being programmed to cause the electrical control circuitry to execute a predetermined sequence of independently applying control signals to adjust the electrical load and the output of the thermoelectric circuit; and
a receiver-transmitter for intercommunicating information between the microcontroller and the computing device.

7. The apparatus according to claim 1, wherein the electrical load comprises:
a plurality of variable resistance channels, each comprising a plurality of resistive elements having respective resistance values, and a plurality of relays associated with respective ones of the resistive elements, wherein the relays are operative, responsively to the control signals of the electrical control circuitry, to respectively connect and disconnect their associated resistive elements; and
a switch for completing a circuit between a selected one of the variable resistance channels and the tissue ablator.

8. The apparatus according to claim 1, wherein the electrical load comprises:
a plurality of resistive elements having respective resistance values; and
electrical connectors associated with respective ones of the resistive elements for connecting selected ones of the resistive elements to the tissue ablator.

9. A method for testing an ablator, comprising: connecting a tissue probe emulator to a tissue ablator being tested, the emulator comprising a temperature sensor, a thermoelectric circuit connected to the temperature sensor and operative to vary an output temperature of the thermoelectric circuit sensed by the temperature sensor, an electrical load configured to be adjustable in response to control signals and electrical control circuitry connected to the thermoelectric unit and the electrical load;

independently applying control signals for adjusting the electrical load and the output of the thermoelectric circuit;

communicating signals emitted by the temperature sensor to the tissue ablator; delivering an ablation energy output of the tissue ablator to the electrical load; and measuring the ablation energy output while performing the step of independently applying control signals for adjusting.

10. The method according to claim 9, wherein the electrical load comprises a plurality of resistive elements having respective resistance values and a plurality of relays associated with respective ones of the resistive elements, the method further comprising, responsively to signals of the electrical control circuitry, actuating the relays to respectively connect and disconnect their associated resistive elements.

11. The method according to claim 10, further comprising the step of connecting the resistive elements relative to a common reference to emulate a unipolar electrode.

12. The method according to claim 10, further comprising the step of connecting the resistive elements relative to one another to emulate a bipolar electrode.

13. The method according to claim 10, wherein the electrical control circuitry comprises a microcontroller and switching transistors connected to the microcontroller and respective ones of the relays, the transistors being responsive to relay control signals of the microcontroller for enabling and disabling the relays.

14. The method according to claim 13, further comprising:

linking a computing device to the electrical control circuitry, the computing device;

executing a program using the computing device to transmit a predetermined sequence for performing the step of independently applying control signals for adjusting; and using a receiver-transmitter for communicate the predetermined sequence from the computing device to the microcontroller.

15. The method according to claim 9, wherein the electrical load comprises a plurality of variable resistance channels, each comprising a plurality of resistive elements having respective resistance values, and a plurality of relays associated with respective ones of the resistive elements, wherein the relays are operative, responsively to control signals of the electrical control circuitry, to respectively connect and disconnect their associated resistive elements; and a switch for completing a circuit between a selected one of the variable resistance channels and the tissue ablator.

16. The method according to claim 9, wherein the electrical load comprises a plurality of resistive elements having respective resistance values, wherein the step of independently applying control signals for adjusting comprises connecting respective ones of the resistive elements to the tissue ablator.

17. The method according to claim 9, further comprising the steps of: monitoring an impedance of the electrical load; and verifying that the ablation energy output varies in a sequence when a limiting condition of the temperature sensed by the temperature sensor or the impedance of the electrical load is violated.

* * * * *